United States Patent [19]

Task et al.

[11] Patent Number: 4,623,258
[45] Date of Patent: Nov. 18, 1986

[54] METHOD FOR MEASURING HAZE IN TRANSPARENCIES

[75] Inventors: Harry L. Task, Dayton; Louis V. Genco, Enon, both of Ohio

[73] Assignee: The United States of America as represented by the Secretary of the Air Force, Washington, D.C.

[21] Appl. No.: 623,667

[22] Filed: Jun. 22, 1984

[51] Int. Cl.[4] .............................................. G01N 21/01
[52] U.S. Cl. .............................................................. 356/432
[58] Field of Search ............... 356/337, 338, 340, 342, 356/445, 446, 447, 448, 215, 221, 236; 250/562, 572

[56] References Cited

U.S. PATENT DOCUMENTS

3,639,112  2/1972  Poola ........................................ 65/29
3,737,665  6/1973  Nagae .............................. 250/219 DF
4,310,242  1/1982  Genco et al. ......................... 356/128
4,400,089  8/1983  Farabaugh ........................... 356/382

Primary Examiner—Bruce Y. Arnold
Attorney, Agent, or Firm—Bobby D. Scearce; Donald J. Singer; John R. Flanagan

[57] ABSTRACT

A method of measuring haze in a transparency includes the steps of illuminating a transparency to be measured from one side using a semi-collimated light source disposed in a predetermined angular relationship to the transparency, measuring the illumination (E) falling on a surface of the transparency from the one side thereof, then along a predetermined line of measurement through the transparency using a photometer to measure the veiling luminance (L) within the transparency from another side of the transparency opposite to the one side thereof, and, finally, calculating the haze index of the transparency by solving $H_i = L/E$.

10 Claims, 4 Drawing Figures

METHOD FOR MEASURING HAZE IN TRANSPARENCIES

RIGHTS OF THE GOVERNMENT

The invention described herein may be manufactured and used by or for the Government of the United States for all governmental purposes without the payment of any royalty.

CROSS REFERENCE TO RELATED APPLICATION

Reference is hereby made to the following co-pending U.S. application disclosing subject matter which is relaed to the present invention: "Method of Measurement of Haze in Transparencies," by Harry L. Task et al, U.S. Ser. No. 463,191, filed Feb. 2, 1983.

BACKGROUND OF THE INVENTION

1. Field of the Invention

The present invention broadly relates to measuring halation in transparencies, such as aircraft windscreens made of plastic or the like, and, more particularly, is concerned with a method for measuring a haze index of transparent materials that can be related to contrast loss when viewing a target through the material.

2. Description of the Prior Art

The most common reasons for removing an aircraft transparency are optical, and the most common optical problem is haze, halation or contrast loss as perceived by the pilot.

The presently accepted method of measuring haze is based on a technique developed at the National Bureau of Standards (NBS). This method has been adopted as a haze measurement standard by the American Society for Testing and Materials (ASTM) and by the U.S. Government. The Gardner Haze Meter is a specific device used to measure haze, since its design is based on this method.

By way of background, light incident on a transparent material can be absorbed, reflected, scattered and transmitted. Since light (energy) must be conserved, the quantities of absorbed, reflected, scattered and transmitted light must add up to the amount of incident light. The scattered and transmitted light are the two parts of interest for measuring haze using the NBS method. In this case the total light that passes through the transparent material is equal to the amount transmitted plus the amount scattered. Only the transmitted portion is usable to form an image of the object from which the light originated; the scattered light has lost its image forming information.

The NBS definition of haze is the ratio of the scattered light to the total light that comes through the transparency (S+T). In equation form:

$$H = \frac{S}{(S + T)} \quad (1)$$

where:
H = haze
S = scattered light
T = transmitted (image forming) light

Values of haze range from 0 (no scattering) to 1 (total scattering). Although the definition seems quite reasonable and the haze values are bounded and well behaved, it is not possible to directly relate the haze value to contrast loss and visual performance degradation. In addition, the instrumentation is designed specifically for relatively small, thin, unscratched, flat samples that can be placed flush with the entrance aperture of the integrating sphere used to make the measurements. The measurements are invalid if made at any angle other than the normal to the surface. Furthermore, the instrumentation is not usable for measuring the haze of an aircraft transparency while it is installed on the aircraft (or under field conditions).

Because of these significant disadvantages, a new technique for measuring and defining haze is needed that can be directly related to contrast loss and observer performance and can be used to measure windscreens while they remain installed on the aircraft.

SUMMARY OF THE INVENTION

The present invention provides a haze measurement method designed to substantially satisfy the aforementioned needs. By more directly and objectively measuring the haze index under controlled conditions similar to those normally encountered during use, predictions can be made as to the effect of the transparency on visual performance. Both volume haze (which remains relatively constant) and surface-induced haze (which increases with surface degradation) may be measured. The invention allows measurement of haze in transparent materials, such as windscreens, in their installed environment and provides the fundamental information required to extrapolate contrast losses to any ambient illumination condition. It can be used on thick, curved and/or tilted materials unlike any of the other methods. Thus, the invention provides a means of characterizing the optical clarity of transparent materials either for initial acceptance testing or later degradation testing. In such capacity, the invention is ideally suited to measuring aircraft windscreens to determine when they should be removed from the aircraft due to excessive loss of visibility through them. Since the same method can now be used during several stages in the manufacturing process and during lifecycle durability testing, correlation of the data is assured.

Accordingly, the present invention broadly provides a method for measuring haze in a transparency which basically includes the steps of: (a) illuminating a transparency to be measured from one side thereof using only a predetermined semi-collimated light source disposed in a predetermined angular relationship to the transparency; (b) measuring the illumination (E) falling on a surface of the transparency from the one side of the transparency; (c) along a predetermined line of measurement through the transparency, measuring the veiling luminance (L) within the transparency from another side of the transparency opposite to the one side thereof; (d) placing a light-absorbing surface on the one side of the transparency along the line of measurement of the veiling luminance through the transparency to ensure that the luminance being measured is only scattered light; and (e) calculating the haze index of the transparency by solving for $H_i$:

$$H_i = \frac{L}{E}.$$

The illumination falling on the one surface of the transparency is measured by using a photometer and a Lambertian reflector. A Lambertian reflector is a surface that reflectively scatters all incident light in a perfectly diffusing manner. By placing the reflector on the one side of the transparency on the surface thereof, the luminance of reflector, equivalent to the illumination of the surface (E), is measured using the photometer. Also, by placing the same photometer on the opposite side of the transparency along the line of measurement, the veiling luminance (L) can be indicated by measuring the values of a black target.

The above-outlined steps are primarily for use in laboratory testing. For field testing of transparencies, actual sunlight, correctly oriented with respect to the transparency, can be used instead of the artificial light source. For both conditions, a combination side-by-side black/white target may be used in the line of measurement of the photometer. First, the transmission coefficient must be measured. This is accomplished using the photometer and the white target area. The luminance (W) of the white target area is measured directly (no transparency is interposed), using the photometer to obtain a reading. Then, the white target area is measured through the transparency to obtained the transmitted luminance (W1). The transparency is shaded from as much ambient illumination as possible to prevent the veiling luminance from contaminating the transmissivity measurement. The transmissivity (t) is then simply the ratio (W1/W) of the photometer reading through the transparency to the reading without the transparency using the white target area. Next, the veiling luminance (L) of the transparency is measured using the black target area. However, since the black area will usually reflect enough light that it must be taken into account, the transmitted luminance value must be removed from the veiling luminance values. This is done by measuring the luminance (B) of the black area directly (not through the transparency) and multiplying it by the transmission coefficient (t) of the transparency and subtracting this luminance value from the measured veiling luminance (L) value.

The haze index can be calculated for the above readings and information by applying them to the following formula:

$$H_i = \frac{L - Bt}{E}.$$

Following thereafter, the contrast of objects viewed through the transparency may be calculated by using the following formula:

$$C = \frac{W - B}{W + B - 2EH_i/t}.$$

Finally, the contrast loss induced by interposing a transparency in the observer's line of sight may be calculated from the following formula:

$$CL = 1 - \frac{M}{M + EH_i/t}$$

where:
CL=contrast loss, and
M=mean luminance of white and black target areas (without the transparency) which is equal to (W+B)/2.

DETAILED DESCRIPTION OF THE PREFERRED EMBODIMENT

New haze measurement technique

Haze in transparencies in the context of the present invention refers to the property that visually corresponds to the loss of available scene contrast which occurs when looking through the transparency. This contrast loss is a result of light scattering into the line of vision, and appears as a veiling luminance. The level of the veiling luminance is proportional to the illumination falling on the surface of the transparency. The haze index provided by the present invention is defined as the proportionality constant that relates the illumination level to the veiling luminance level; in equation form:

$$H_i = \frac{L}{E} \qquad (2)$$

where
$H_i$=haze index
L=veiling luminance
E=illumination at surface of transparency.

The value of the haze index is in units of luminance/illuminance such as ft.-Lamberts per ft.-candle. It should be noted that the haze value is highly dependent on the geometry of the illuminating source and the angle of view through the transparency. This may at first seem to be a disadvantage of this method over the non-directional NBS haze method. It is certainly less convenient; however, it does directly relate with visibility through the transparency which also varies with the illuminating and viewing geometry.

The haze index provided by the present invention can be measured both in laboratory testing and in field testing using similar techniques. The laboratory testing technique yields a haze index in a straight forward manner whereas the field testing method and system require a certain level of calculation to obtain the haze index.

Figure 1A:
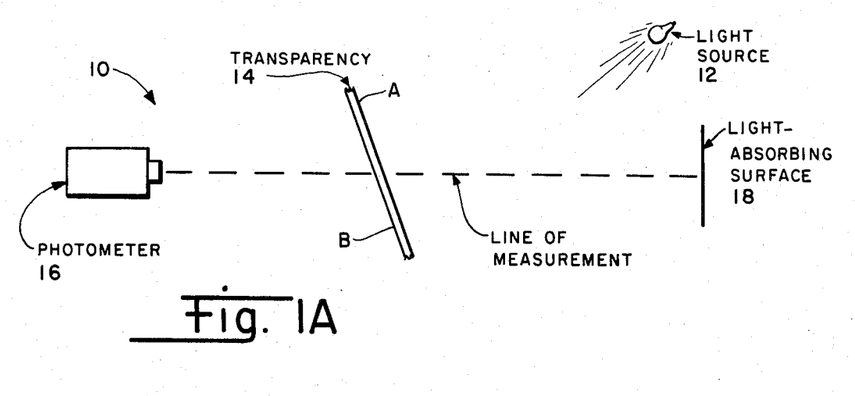
FIGS. 1A and 1B are schematical views of the system for carrying out the haze index measurement method of the present invention adapted for laboratory testing of transparencies.
Figure 1B:
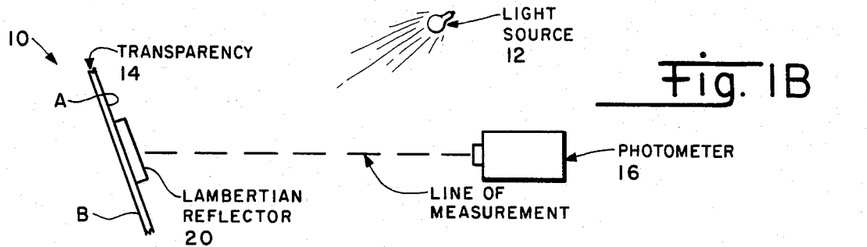

FIGS. 1A and 1B show a system, generally designated 10, for carrying out the haze measurement method of the present invention, adapted for laboratory testing of transparencies. For laboratory measurement a semi-collimated light source 12 is used to illuminate the transparency 14 to be measured. As seen in FIG. 1A, photometer 16 is used on the opposite side of the transparency 14 to measure the veiling luminance within the transparency. If the transparency has any haze effects, illumination of the transparency from side A will give rise to luminance L at opposite side B which will appear to be emanating from the transparency. A black, light-absorbing surface 18 must be placed along the line of measurement of the photometer 16 to ensure that the luminance being measured is only the scattered light and not a combination of scattered and transmitted light. The method is carried out in a light controlled room with only the single light source 12 turned on.

The illumination falling on the surface A of the transparency 14 can be measured using the same the photometer 16 by making use of a Lambertian reflector 20, as seen in FIG. 1B. A Lambertain reflector is a surface that reflectively scatters all incident light in a perfectly diffusing fashion. Because of the way in which ft.-candles (illumination) and ft.-Lamberts (luminance) are defined, the luminance of a perfectly diffusing reflector in ft.-Lamberts is numerically equivalent to the illuminance in ft.-candles falling on the surface. Thus, one can place a Lambertain reflector (such as barium sulphate) on the surface of interest, such as surface A, and measure its luminance in ft.-Lamberts which is numerically equal to the illumination on the surface in ft.-candles.

Once the veiling luminance and the illumination are measured, the haze index is calculated using equation (2) above. To fully characterize the transparency 14, the haze index would be measured for all illumination and viewing angles of interest.

Figures 2A, 2B:
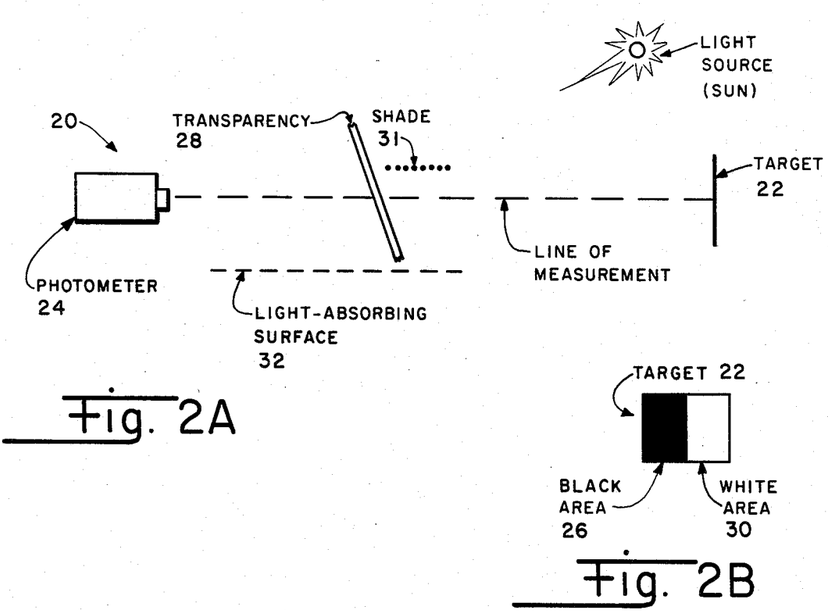
FIGS. 2A and 2B are schematical views of another system for carrying out the haze index measurement method adapted for field testing of transparencies.

FIGS. 2A and 2B show another form of a system, generally designated 20, for carrying out the haze measurement method of the present invention, adapted for field testing of transparencies. The haze index is measured on installed aircraft transparencies in a manner similar to that used in the laboratory with some minor modifications. Instead of using an artificial light source, one can use actual sunlight if the sun is oriented correctly for the desired measurement.

Also, in this version a combination side-by-side black/white target 22, as also seen in FIG. 2B, is used in the line of measurement of the photometer 24. A flat black area 26 of the test target 22 (which is used as a light trap) will usually reflect enough light that it must be taken into account when calculating the haze index. This is done by measuring the luminance of the black area 26 directly (not through the transparency, such as a windscreen 28), multiplying it by the transmission coefficient of the transparency 28 and subtracting this luminance from the measured veiling luminance. This has the effect of removing the transmitted luminance from the veiling luminance reading. Therefore, the haze index in equation form is:

$$H_i = \frac{L - Bt}{E} \quad (3)$$

where
$H_i$ = haze index
$L$ = veiling luminance measurement
$B$ = luminance of the black target area without the transparency
$E$ = illumination at surface of transparency
$t$ = transmission coefficient of the transparency.

Note that equation (3) reduces to equation (2) when the luminance of the black target area 26 is very low (i.e. B approaches 0).

It is evident from equation (3) that it is also necessary to measure the transmission coefficient of the transparency in order to obtain accurate results. The transmission coefficient can be measured easily using the same photometer 24 and a flat white area 30 of the target 22. The luminance of the white target area 30 is measured directly (no transparency 28 interposed), same as in case of black target area, using the photometer 24 to obtain a baseline reading. Then, the white target area 30 is measured through the transparency 28 to obtain the transmitted luminance. However, care must be taken to ensure that the transparency is shaded from as much ambient illumination as possible by interposing a shading surface 31 (as represented by the dotted line in FIG. 2A) and reflections should be minimized by using a flat black, light-absorbing surface 32 (as represented by the dashed line in FIG. 2A). The transparency is shaded to prevent the veiling luminance from contaminating the transmissivity measurement. The transmissivity is then simply the ratio of the photometer reading through the transparency to the reading without the transparency. The transmissivity is a critical parameter in calculating the contrast loss through the transparency as will now be described.

Contrast loss due to haze

It will be recalled that the purpose of the present invention is to provide a method of haze index measurement that can be related to contrast loss when viewing a target through a transparent material. In the description which follows, the mathematical relationship between the haze index as determined by the method of the present invention and contrast loss will be demonstrated.

For simplicity of calculation, it will be assumed that the target of interest is a black area next to a white area on a target similar to the target 22 of FIG. 2B used for measuring haze index and transmissivity. The contrast of such a target is defined in equation (4):

$$C1 = \frac{W - B}{W + B} \quad (4)$$

where:
$C1$ = contrast of target
$W$ = luminance of the white area
$B$ = luminance of the black area If this same target is now viewed through a transparency that has some level of haze caused by ambient illumination, then the apparent contrast of this target will change. Two effects take place: first, each luminance level within the target is reduced by the transmission coefficient of the transparency and, second, a veiling luminance is added to both luminance levels of the target. The resulting apparent target luminances are therefore:

$$W' = Wt + L \quad (5)$$

and $$B' = Bt + L \quad (6)$$

where:
$W'$ = luminance of white area viewed through transparency
$B'$ = luminance of black area viewed through transparency
$t$ = transparency transmissivity
$L$ = veiling luminance
$W$ = luminance of white area without transparency
$B$ = luminance of black area without transparency.

These values can be substituted into the general equation for contrast to obtain the contrast as viewed through the transparency:

$$C2 = \frac{W' - B'}{W' + B'} = \frac{(Wt + L) - (Bt + L)}{(Wt + L) + (Bt + L)}. \quad (7)$$

Equation (7) can be further reduced by dividing the numerator and denominator by t and by substituting equation (2) for the veiling luminance. This results in the following equation:

$$C2 = \frac{W - B}{W + B + 2EH_i/t} \quad (8)$$

Note that equation (8) for C2 is similar to equation (4) for C1 with the exception of the extra term in the denominator. It is this term that results in the lowered contrast when viewing through the transparency. Part of this term is sufficiently important that it should have its own identifying name. The value of $H_i/t$ is a basic characteristic that depends only on the transparency material involved and not on the ambient conditions (E;illumination). It is therefore ideally suited for comparing transparency haze effects of materials. For this reason, the value of $H_i/t$ is referred to as the "haze ratio":

$$\text{haze ratio} = V_r = \frac{\text{haze index}}{\text{transmissivity}} = \frac{H_i}{t} . \quad (9)$$

Before deriving the equation for the contrast loss, it will be helpful if the equations for contrast are put in a slightly different form. First, define the amplitude of the contrast as half the difference between the white and black targets and, secondly, define the means target luminance as half of the sum of the white and black targets. In equation form:

$$\text{amplitude} = A = (W - B)/2 \quad (10)$$

and $$\text{mean} = M = (W + B)/2. \quad (11)$$

If equations (10) and (11) are substituted into equations (4) and (8), one obtains:

$$C1 = A/M \quad (12)$$

and $$C2 = \frac{A}{M + EH_i/t} . \quad (13)$$

The loss in contrast is given in equation (14):

$$CL = (C1 - C2)/C1 \quad (14)$$

where
CL=contrast loss
C1=target contrast viewed directly
C2=target contrast viewed through transparency.
Substituting equations (12) and (13) into equation (14), one obtains:

$$CL = 1 - \frac{M}{M + EH_i/t} . \quad (15)$$

Equation (15) is the primary equation for predicting the resulting contrast loss for any mean target luminance and ambient illumination condition. It is particularly important to note that the result of equation (15) is independent of the target contrast but only depends on the average luminance of the target. Another important fact is that if the haze index is not zero, then the contrast loss also depends explicitly on the transmission coefficient of the transparency. This is a significant result in that typically one does not expect a drop in transmissivity to cause a loss of contrast.

Experiments to demonstrate the validity of the method of the present invention were carried out on aircraft windscreens and HUDs (heads-up displays). Four measurements were made: actual contrast loss, haze index, ambient illumination and transmissivity. The latter three measurements were used to calculate the predicted contrast loss using equation (15) to compare with the measured actual contrast loss. It was not always possible to measure the transmissivity due to lack of convenient means of shading the transparency from direct sunlight. For data sets where the transmissivity was not measured directly, the transmissivity was estimated from previous lab data for the type of transparency involved. With respect to several uninstalled windscreens, one glass and the remainder plastic, and several HUDs, the predictive capability of the haze index method of the present invention appears reasonable with acceptable errors between predicted and measured values of contrast loss. From the results of the experiments, it was quite apparent that the haze index measurement method of the present invention provides a nearly ideal approach to quantifying and predicting contrast losses in aircraft transparencies due to light scatter. The method can be used in the lab or in the field on almost any type of transparency. Aircraft windscreens and HUDs were the primary transparencies of interest in the experiments; however, the method applies equally well to visors, chemical defense masks, eyeglasses, auto windscreens, etc.

The following appendix contains a description of the new proposed "Standard Method for Measurement of Haze Index", in accordance with the present invention, which is intended for use by personnel who will carry out the measurement procedures. It is being included herein to supplement the detailed description of the present invention so as to enhance the ability of one skilled in the art to perform the method of the present invention and provide more specific information concerning the best mode of the invention disclosed hereinbefore.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

APPENDIX

Standard Method For Measurement Of Haze Index

1. SCOPE

This is an objective method for determining the amount of halation (sometimes called haze, veiling glare or contrast loss) imposed by transparent parts such as aircraft windscreens and canopies. The method may be applied to any shape or thickness part, and is intended to accurately determine one of the optical effects of surface degradation of the transparency. Instructions are given for both laboratory and field versions of the method. The results correlate with visual performance metrics, such as detection of objects in near or distant airspace. As such, the method may be used to determine the effect of ageing transparencies on visual performance for targets external to the aircraft and may have significant safety implications.

2. SUMMARY OF THE METHOD 2.1. Using a specified light source, photometer, and Barium Sulphate chamber, and with the part held in its installed position, the illumination impingent on the outer surface of the part is measured. A second series of measurements is taken through the transparency at specified look and illumination angles with the same photometer and a specified target external to the transparency. A third series of measurements is taken with similar angular considerations, but without the transparency.

2.2. The data from these measurements are then mathematically reduced to yield a number (the haze index) for the transparency. This index differs from haze values measured by other instruments in that it is directly related to both visual performance and acceptance by individuals viewing objects through the transparency. Use of this index and appropriate tables will yield effective visual detection range through the portion of the transparency being measured.

3. SIGNIFICANCE AND USE 3.1. Studies have shown that the most common reasons for removing an aircraft transparency are optical, and the most common optical problem is haze, halation or contrast loss as perceived by the pilot. Present methods of measuring haze are restricted to relatively small thin, flat parts, whose surfaces are scratch and abrasion free. The measurements are invalid if made at any angle other than the normal to the surface, and the results are not directly correlated with the visual effects as experienced by the observer. Furthermore, the device commonly and presently used to measure haze is not useable under field conditions on installed aircraft transparencies.

3.2. The method and apparatus described herein overcome all the problems listed above. By more directly and objectively measuring the haze index under controlled conditions similar to those normally encountered during use, predictions can be made as to the effect of the transparency on visual performance. Both volume haze (which remains relatively constant) and surface-induced haze (which increases with surface degradation) may be measured. Since the same method may now be used during several stages in the manufacturing process and during lifecycle durability testing, correlation of the data is assured.

3.3. Because of the advantages of this method, it may be used for aiding in determination of visibility through aircraft transparencies after exposure to extreme environmental conditions or chemical attack which may degrade the optical clarity of the part.

4. TERMINOLOGY 4.1. Haze: The spatial attribute of smokiness or dustiness which interferes with clear vision. The ratio of diffuse to total transmittance of a beam of light.

4.1.1. Surface Haze: That portion of haze caused or induced by properties or degradations of the surface of transparent parts.

4.1.2. Volume Haze: That portion of haze caused or induced by properties or degradations of the material bounded by the two major surfaces of transparent parts.

4.2. Halation: A spreading of light beyond its proper boundaries. Often a synonym for haze.

4.3. Contrast: The ratio or other numerical representation of the difference in photometric brightness between two stimulus fields or surfaces.

4.4. Glare: The dazzling sensation of relatively bright light which interferes with optimal vision.

4.4.1. Veiling Glare: Glare produced by excess light uniformly distributed over the visual field so as to cause reduced contrast and therefore reduced visibility.

4.5 Illuminance: The internationally accepted photometric term for the intensive property of the luminous flux passing through a cross section of a beam, or falling on an illuminated surface. Units: lumens per sq. foot (foot-candle) or lumens per sq. meter (lux).

4.6. Luminance: The internationally accepted photometric term for the intensive property of an emitting, transmilluminated or reflecting surface (formerly called brightness). The luminous flux emitted, transmitted or reflected per solid angle per unit projected area of the surface. Units: foot-lambert, millilambert, or candle/sq. meter (nit).

4.7 Haze Index: The ratio of corrected Veiling Luminance created by the transparency to the illumination impingent on its surface.

4.8. haze Ratio: The ratio of Haze Index to transmission coefficient (measured at installed angle). A number indicating relative clarity of a transparent part.

5. APPARATUS 5.1. A portable photometer capable of accurately measuring luminances over the range of 0.1 cd/m$^2$ to 5000 cd/m$^2$, and with a spot size of 0.33 to 1 degree (similar to a Minolta Spot Luminance Meter).

5.2. A Barium Sulphate chamber, having an effective Lambertian reflectance. This chamber or target is used to determine the illumination impingent on the surface of the transparency.

5.3. An aluminum backed target (approximately $\frac{1}{8}$ inch thick), one half of which consists of a matte white finish (several coats of Titanium White paint, evenly applied with a spary gun over an appropriate primer or base coat); the other half consisting of a highly absorbent material (flat black velvet or similar material). The target size is approximately two feet wide and one foot high, hinged in the middle for convenience.

5.4. A standardized illumination source in such a manner as to evenly and constantly illuminate the surface of the part under test. The intensity of this source is relatively unimportant as long as it is not in the lower range of the photometer being used.

5.4.1. For outdoor field tests, this illumination source may be provided by the Sun, recognizing that scattered or uneven cloud cover will reduce the constancy of illumination during the duration of the procedure, and affect results. Day to day variations in intensity are unimportant as they will be compensated in the measurement of the test target—relative contrast, not absolute illumination of the transparency is critical.

5.4.2. For indoor test facilities, the illumination source may be provided by two sets of photographic floodlamps: one nearly collimated beam being used to illuminate the transparency, and the other used to illuminate the target. The illumination level of the transparency under test should be approximately ten times that of the target.

5.5. A solar inclinometer or other apparatus for accurately determining the illumination angle with respect to true horizontal.

6. TEST SPECIMEN 6.1. The part to be tested should be positioned in such a manner as to approximate its installed configuration. No special conditioning other than cleaning is required. If the part is not cleaned, accurate results will still be acquired, but they will indicate the contrast loss imposed by both the specimen and the surface contamination.

7. CALIBRATION AND STANDARDIZATION 7.1. The calibration of the photometer and Barium Sulphate cell should be done according to the instructions accompanying the devices.

7.2. The contrast of the two halves of the aluminum-backed target, as measured with the above photometer should be greater than 90%. Target contrast may be determined by measuring each side of the target with the photometer, using either diffuse natural or artificial illumination. The results of the measurements of the dark and light halves may then be applied to the formula found in Section 9. Neither test distance nor illumination are critical, as long as the readings are above the lowest range sensitivity of the photometer.

7.3. The light source used to illuminate the transparency will be placed at an user-specified elevation and azimuth angle with respect to the surface of the transparency. If natural sunlight is used under field conditions, the measurement must be taken at an appropriate time of day to approximate this condition. Since haze index will vary as a function of these angles, they must be standardized for any specific application.

7.3.1. For full scale transparencies, the illumination angle should correspond to near worst-case conditions, i.e. flying toward the Sun.

7.3.2. For test coupons, the coupon will be mounted so the illumination angle is perpendicular to the surface of the coupon, and the observation angle is 60 degrees to the normal. The lines bounding these angles will all lie in the same plane.

7.4. The photometer will be placed at "design eye" position for the transparency under consideration. If this position obviates comfortable use of the instrument with seat fully retracted, an alternate position as close as possible to design eye may be specified.

8. PROCEDURE 8.1. Typical procedure to follow for field (outdoor) measurements:

8.1.1. For measurements made in the Northern Hemisphere, position the aircraft or transparency so it is facing into the Sun. The Sun should be less than 5 degrees to the left or centerline, and moving toward the right side of the aircraft. Sun elevation as measured with the Solar Inclinometer should be consistent from measurement to measurement if these measurements are to be compared. This elevation may be specified by the using agency. If measurements are made in the Southern Hemisphere, reverse "right" and "left" above.

8.1.2. Place the Barium Sulphate cell on the outside surface of the transparency at a location corresponding to the intersection of the line of sight with the transparency surface. The surface of the cell should be parallel to the surface under measurement.

8.1.3 Use the photometer and Barium Sulphate cell to determine the illumination on the transparency by reading the reflected light at an approximate normal to the Barium Sulphate cell. Record this number as "E".

8.1.4. Position the photometer so that it is close to design eye position, yet can look around the transparency. Take a reading of the dark side of the target. Record this reading as "B".

8.1.5. Position the photometer so that it is close to design eye position, but now looks through the transparency. Take a reading of the dark side of the target. Record this reading as "L".

8.2. Procedure to follow for indoor measurements:

8.2.1. Position the floodlamp so it is directly facing the transparency. The lamp should be elevated approximately 60 degrees, and on a line corresponding to the centerline of the aircraft. The light should be partially collimated.

8.2.2. Repeat the steps found in paragraphs 8.1.3 through 8.1.5 above.

9. CALCULATIONS 9.1. Haze Index may be calculated from the above information by applying the data to the following formula:

$$H_i = \frac{L - Bt}{E}$$

where
$H_i$ = haze index
L = veiling luminance measurement (luminance of black target through transparency)
B = luminance of the black target (without transparency)
E = illumination at surface of transparency
t = transmission coefficient of transparency.

9.3.1. The transmission coefficient of the material under test may be determined by reference to appropriate handbooks or by direct measurement using ASTM Method D 1003-6170 (Haze and Luminous Transmittance for Transparent Plastics, Mar. 4, 1975), or by the following method:

9.3.1.1. Using a photometer, first measure the luminance of the white side of the standard target with no transparency interposed in the optical path. Remeasure the target with the transparency interposed, and assuring that the transparency is shaded from as much ambient illumination as possible, and reflections are minimized by covering reflective surfaces with a flat black, light absorbing cloth. A long tube whose inner surface has been coated with flat black paint may be used between the photometer and the surface of the transparency to further reduce the chances of stray light from interfering with the measurement.

9.3.1.2. Transmissivity may then be calculated from the following formula:

$$t = W1/W$$

where:
W = photometer reading with no transparency
W1 = photometer reading with transparency.

9.3.2. The contrast of objects viewed through the transparency may be determined by using the following formula:

$$C = \frac{W - B}{W + B + 2EH_i/t}$$

where:
C = contrast
$H_i$ = haze index
W = luminance of the white target (without transparency)
B = luminance of the black target (without transparency)
E = illumination at surface of transparency
t = transmission coefficient of transparency.

9.3.3. The term $H_i/t$ in the above formula is referred to as the "haze ratio". It is ideally suited for the comparison of transparency haze in various materials since it depends only on the optical quality of the material involved and not on the ambient conditions.

$$H_r = H_i/t$$

where:
$H_r$ = haze ratio
$H_i$ = Haze index
$t$ = transmission coefficient.

9.3.4. The contrast loss induced by interposing a transparency in the observer's line of sight may be determined from the formula:

$$CL = 1 - \frac{M}{M + EH_i/t}$$

where:
CL = contrast loss
M = mean luminance of white and black sides of target (without transparency) = (W + B)/2
$H_i$ = haze index
E = illumination at surface of transparency
t = transmission coefficient of transparency.

10. PRECISION AND ACCURACY 10.1. There may be some differences in contrast loss, comparing the right and left sides of bubble transparency. These differences may be due to real differences in contrast levels as measured through the transparency. Contrast level is affected not only by halation induced during transmission, but by veiling glare caused by reflections from aircraft glare shields or indoor holding fixtures. Asymmetric readings, if found, are real, and will be experienced under the particular measurement conditions during the test. If, while performing the test, a significant veiling glare contribution may be attributed to cockpit reflections, and if it is desired that the effects of this parameter be reduced, the offending reflective surface should be covered with a non-reflecting cloth or other material, and an average of right and left side readings may be taken.

10.2 Accuracy of the haze index findings is primarily a function of the accuracy of the photometer and constancy of illumination during test readings. Another major factor is the transmission coefficient of the transparency under test. Slight misposition of the external target will result in only minor errors, as will contrast differences among test targets. An accuracy check (to determine constancy of illumination) may be made by determining the baseline illumination of the Barium Sulphate cell several times during the normal test run. These values should not differ by more than 5.0%.

10.3. One possible significant source of differences among measurement values is the use of different illumination or viewing angles across measurements. As indicated above, this method is highly sensitive to the angles involved, and such angles should be specified for each particular application; the angles approaching that of the worst situation usually encountered when viewing through the transparency.

Having thus described the invention, what is claimed is:

1. A method of measuring haze in a transparency, comprising the steps of:
    (a) illuminating a first surface of a transparency from one side thereof using a source of light disposed in a predetermined angular relationship to a predetermined line of measurement through said transparency;
    (b) measuring the illumination from said source at said first surface of said transparency;
    (c) at a point along said predetermined line of measurement through said transparency and on the side opposite said one side, measuring the luminance of said transparency resulting only from said illumination of said first surface, whereby light traveling from said one side of said transparency along said predetermined line of measurement and through said transparency is excluded to ensure that the luminance being measured results only from scattered light; and
    (d) calculating a haze index of said transparency by solving for $H_i$:

$$H_i = L/E$$

where:
$H_i$ = haze index of said transparency,
L = luminance of said transparency resulting from said illumination of said first surface, and
E = illumination at said first surface of said transparency.

2. The haze measuring method as recited in claim 1, wherein the step of measuring the illumination falling on a first surface of said transparency from said one side includes:
    placing a Lambertian reflector on said first surface, said reflector producing a diffuse scattering of all incident light thereon in such manner that its luminance is equivalent to the illumination of said surface; and
    measuring the luminance of said reflector.

3. The haze measuring method as recited in claim 2, wherein the luminance of said reflector is measured using a photometer.

4. The haze measuring method as recited in claim 1, wherein the luminance of said transparency is measured by a photometer placed at said point along said predetermined line of measurement.

5. The haze measuring method as recited in claim 1, wherein said light source is partially collimated.

6. A method of measuring haze in a transparency, comprising the steps of:
    (a) illuminating a first surface of a transparency to be measured from one side thereof using a source of light disposed in a predetermined angular relationship to a predetermined line of measurement through said transparency;
    (b) measuring the illumination from said source at said first surface of said transparency;
    (c) at a point along said predetermined line of measurement through said transparency and opposite said first surface, measuring the luminance of said transparency resulting from said illumination of said first surface, said measuring including
        (i) placing a black target along said predetermined line of measurement on said one side of said transparency,
        (ii) measuring the luminance of said black target through said transparency, and
        (iii) measuring the luminance of said black target directly without the transparency; and
    (c) calculating a haze index of said transparency by solving for $H_i$:

$$H_i = \frac{L - Bt}{E}$$

where:
- $H_i$ = haze index
- L = luminance of the black target as measured through said transparency
- B = luminance of the black target without said transparency
- E = illumination at said first surface of said transparency
- t = known transmission coefficient of said transparency.

7. The haze measuring method as recited in claim 6, further comprising:
(e) along said predetermined line of measurement through said transparency, measuring said transmission coefficient of said transparency including:
(i) placing a white target along said predetermined line of measurement on said one side of said transparency,
(ii) measuring the transmitted luminance of said white target through said transparency,
(iii) measuring the luminance of said white target without said transparency, and
(iv) calculating said transmission coefficient by dividing said transmitted luminance of said white target by said luminance of said white target without said transparency.

8. The haze measuring method as recited in claim 7, wherein said light source is the sun.

9. The haze measuring method as recited in claim 8, wherein said transmission coefficient measuring further includes:
(v) shading said transparency from as much of said illumination of said sun as possible to prevent said luminance of said transparency resulting from said illumination of said first surface from affecting said transmissivity measurement.

10. The haze measuring method as recited in claim 7, wherein the contrast loss of said transparency is calculated by solving for CL:

$$CL = 1 - \frac{M}{M + EH_i/t}$$

where:
- CL = contrast loss of said transparency,
- M = mean luminance of white and black targets without said transparency, (W+B)/2,
- $H_i$ = haze index of said transparency,
- E = illumination at said first surface of said transparency,
- t = transmission coefficient of said transparency.

* * * * *

UNITED STATES PATENT AND TRADEMARK OFFICE
CERTIFICATE OF CORRECTION

PATENT NO. : 4,623,258

DATED : November 18, 1986

INVENTOR(S) : Harry L. Task et al

It is certified that error appears in the above-identified patent and that said Letters Patent is hereby corrected as shown below:

```
Column 1, line 15, "relaed" should be ---related---.
Column 2, line 60, "solveing" should be ---solving---.
Column 3, line 16, "cent" should be ---cient---.
Column 7, line 26, "means" should be ---mean---.
Column 10, line 13, "transmilluminated" should be
---transilluminated---.
Column 10, line 21, "haze" should be ---Haze---.
Column 10, line 36, "spary" should be ---spray---.
Column 10, line 41, after "source" should appear
---arranged---.
Column 11, line 26, a space should appear between "7.3.1." and
"For".
Column 11, line 45, "or" should be ---of---.
Column 13, line 28, in the second line of paragraph numbered
"10.1.", ---a--- should appear in front of "bubble".
Column 14, line 67 (in claim 6), "(c)" should be ---(d)---.
```

Signed and Sealed this

Tenth Day of May, 1988

*Attest:*

DONALD J. QUIGG

*Attesting Officer*          *Commissioner of Patents and Trademarks*